(12) United States Patent
Dehmeshki

(10) Patent No.: US 7,313,261 B2
(45) Date of Patent: *Dec. 25, 2007

(54) USER INTERFACE FOR COMPUTED TOMOGRAPHY (CT) SCAN ANALYSIS

(75) Inventor: Jamshid Dehmeshki, London (GB)

(73) Assignee: Medicsight PLC (GB)

( * ) Notice: Subject to any disclaimer, the term of this patent is extended or adjusted under 35 U.S.C. 154(b) by 0 days.

This patent is subject to a terminal disclaimer.

(21) Appl. No.: 11/295,435

(22) Filed: Dec. 7, 2005

(65) Prior Publication Data

US 2006/0083417 A1      Apr. 20, 2006

Related U.S. Application Data

(63) Continuation of application No. 10/978,369, filed on Nov. 2, 2004, now Pat. No. 7,149,334.

(30) Foreign Application Priority Data

Sep. 10, 2004    (GB) ................ 0420147.1

(51) Int. Cl.
*G06K 9/00* (2006.01)
*G06K 9/40* (2006.01)
*G06K 9/32* (2006.01)

(52) U.S. Cl. .................. 382/131; 382/260; 382/254

(58) Field of Classification Search ............. 382/131, 382/132, 133, 128, 130, 294, 254, 260, 266; 345/156, 792, 793; 128/920, 922; 378/28, 378/37, 62, 98, 63
See application file for complete search history.

(56) References Cited

U.S. PATENT DOCUMENTS 5,761,334 A    6/1998   Nakajima et al.

5,982,917 A   11/1999   Clarke et al.

(Continued)

FOREIGN PATENT DOCUMENTS

EP        0 616 290 A2     9/1994

(Continued)

OTHER PUBLICATIONS

European Search Report issued Jul. 4, 2005 for Application. No. EP 05 25.1836, four pages.

(Continued)

*Primary Examiner*—Yon J. Couso
(74) *Attorney, Agent, or Firm*—Sterne, Kessler, Goldstein & Fox

(57) ABSTRACT

An enhanced image is based on an original image. For instance, the original image can be processed using a filter to provide the enhanced image. The original and enhanced images can be displayed side by side or alternately to facilitate a comparison of the original and enhanced images. A user can change one or more enhancement parameters associated with the enhanced image. For example, the user can change the one or more enhancement parameters while viewing the original and enhanced images to determine an effect the change has on the enhanced image. The user can compare the effect of the changed enhancement parameters with his or her own analysis of the original image. The changed enhancement parameters may be applied to other parts of the original image so as to provide a more accurate analysis of those parts.

14 Claims, 8 Drawing Sheets

U.S. PATENT DOCUMENTS

| | | |
|---|---|---|
| 5,987,345 A | 11/1999 | Engelmann et al. |
| 6,058,322 A | 5/2000 | Nishikawa et al. |
| 6,266,435 B1 | 7/2001 | Wang |
| 6,574,357 B2 | 6/2003 | Wang |
| 6,697,506 B1 | 2/2004 | Qian et al. |
| 6,789,069 B1 | 9/2004 | Barnhill et al. |
| 6,909,913 B2 | 6/2005 | Vining |
| 7,006,862 B2 | 2/2006 | Kaufman et al. |
| 2003/0016850 A1 | 1/2003 | Kaufman et al. |
| 2003/0095697 A1 | 5/2003 | Wood et al. |
| 2004/0047497 A1 | 3/2004 | Daw et al. |

FOREIGN PATENT DOCUMENTS

| | | |
|---|---|---|
| JP | 02 185240 A | 7/1990 |
| WO | WO 02/056240 A1 | 7/2002 |
| WO | WO 03/042921 A1 | 5/2003 |
| WO | WO 03/077203 A2 | 9/2003 |

OTHER PUBLICATIONS

Patent Abstracts of Japan, vol. 1999, No. 6 (Mar. 31, 1999), English Language Abstract for JP Patent Application No. 02 185240 A (Jul. 19, 1990) (Document FP1 on accompanying SB-08A form).

United Kingdom Search Report issued Jan. 6, 2005 for Application No. GB 0420147.1.

Agatston et al., "Quantification of Coronary Artery Calcium Using Ultrafast Computed Tomography," Journal of the American College of Cardiology, Mar. 1990, pp. 827-832.

International Preliminary Report on Patentability issued Mar. 22, 2007 for PCT/GB2005/002953, 7 pages.

USER INTERFACE FOR COMPUTED TOMOGRAPHY (CT) SCAN ANALYSIS

RELATED APPLICATIONS

This application is a continuation of U.S. application Ser. No. 10/978,369, filed Nov. 2, 2004, now U.S. Pat. No. 7,149,334, which claims the benefit of the filing date of GB Patent Application No. 0420147.7, filed Sep. 10, 2004, both of which are incorporated herein by reference in its entireties.

BACKGROUND OF THE INVENTION

1. Field of the Invention

The present invention relates generally to computed tomography (CT), and more particularly to a user interface for displaying an enhanced CT scan image.

2. Background

In conventional analysis of CT images, a radiologist visually inspects each slice of a CT scan, using his or her expertise to identify abnormalities and to distinguish them from normal structures. The task can be made easier by storing the scan image on a computer and providing a user interface that allows the user to move rapidly between slices and visualize the structures in different ways. However, the process is time consuming and must be performed with great care to avoid overlooking abnormalities.

To replace some or all of the work of the radiologist, Computer Assisted Detection (CAD) software has been designed to analyze the scan image and to detect potential lesions. The detection of a lesion can be performed semi-automatically, with some interaction with the radiologist, or automatically, involving no interaction beyond the selection of the image to be analyzed. For example, the applicant's MedicHeart™, MedicLung™, and MedicColon™ diagnostic software perform semi-automatic diagnosis using CT scans of the heart, lung, and colon, respectively.

In practice, the results of CAD can be checked by a radiologist as a safeguard. If the software is used as the 'first reader', the radiologist generally only verifies the results produced by the software and does not analyze the original CT scan. To be effective as a 'first reader', the software needs both high sensitivity (i.e., a low percentage of missed lesions) and high specificity (i.e., a low percentage of false positives), because the radiologist may make medically important decisions based on the results. Using software as a 'first reader' can save substantial time of the radiologist, though achieving both high sensitivity and high specificity can pose a significant challenge.

Alternatively, the software can be used as a 'second reader', where the radiologist makes a preliminary diagnosis based on the original images, and then runs the software as a check for any missed lesions. When used as a 'second reader', the software typically does not save time, but can assist the radiologist in making better diagnoses. The software does not need to have particularly high sensitivity or specificity, so long as it leads to more accurate diagnoses than an unassisted radiologist. Used in this way, the software is analogous to a spelling or grammar checker for word-processing. For instance, the software merely draws the user's attention to oversights, rather than replacing the actions of the user.

What is needed is a user interface for analysis of CT scans that does not need to be as accurate as 'first reader' software and saves more time than 'second reader' software.

PCT patent application WO 03/077203 discloses a user interface that allows corresponding areas from different scans to be displayed side-by-side.

A further problem is that many CAD algorithms rely on a predefined set of parameter ranges for detection of abnormalities. For example the Agatston method, as originally described in 'Quantification of coronary artery calcium using ultrafast computed tomography', Agatston A S, Janowitz W R, Hildner F J et al., J Am Coll Cardiol 1990 15:827-832, applies a threshold of 130 Hounsfield units (HU) to the CT image, and identifies all pixels above that threshold as containing calcium. A scoring system is then used to rate the severity of the calcification, based on the number of pixels above the threshold multiplied by a weight based on the highest intensity within the calcification. If the highest intensity is between 130 and 200 HU, then the weight is 1; if between 200 and 300 HU, the weight is 2; and if over 300 HU, the weight is 3. The values of the threshold and the weights are based on empirical studies of coronary scans and the subsequent outcome for the patients. However, there is continuing debate as to which parameter ranges give the most accurate results. Different ranges may be appropriate for different scan images.

U.S. Pat. No. 6,058,322 discloses an interactive user modification function in which software displays detected microcalcifications and a user may then add or delete microcalcifications. The software modifies its estimated likelihood of malignancy accordingly.

SUMMARY OF THE INVENTION

According to an embodiment of the invention, a method of displaying a CT scan image includes displaying an original scan image and displaying an enhanced scan image derived from the original scan image. The original and enhanced images can be displayed with similar image attributes, such as size and scale, to facilitate comparison between the original and enhanced images. The enhanced image may be enhanced to facilitate identification of lesions or abnormalities in the original image.

In an embodiment, the original and enhanced images are displayed simultaneously. In another embodiment, the original and enhanced images are displayed alternately with a similar size, scale, and position.

An advantage of these embodiments is that the original image can be visually checked with respect to the enhanced image without the enhanced image obscuring features of the original image. Instead of using the enhanced image as a first or second reader, the enhanced image acts as a joint reader with a user. For example, the user can examine the original image while using the enhanced image for assistance.

According to an embodiment, the user is able to change enhancement parameters of the enhanced image while viewing the original and enhanced images. For instance, the user can adjust the enhancement parameters to provide suitable enhancement parameters. The user can adjust the enhancement parameters while observing the effect on the enhanced image. The user can compare the effect with the user's own analysis of the original image. The adjusted enhancement parameters may be applied to other parts of the original image to provide a more accurate analysis of the other parts.

BRIEF DESCRIPTION OF THE DRAWINGS

The present invention is described with reference to the accompanying drawings. In the drawings, like reference numbers indicate identical or functionally similar elements.

Additionally, the left most digit(s) of a reference number identifies the drawing in which the reference number first appears.

DETAILED DESCRIPTION OF EMBODIMENTS OF THE INVENTION

Scan Image

A computed tomography (CT) image can include a plurality of slices, which are generally obtained from a CT scan of a human or animal patient. Each slice is a 2-dimensional digital grey-scale image of the x-ray absorption of the scanned area. The properties of the slice depend on the CT scanner used. For example, a high-resolution multi-slice CT scanner may produce images with a resolution of 0.5-0.6 mm/pixel in x and y directions (i.e., in the plane of the slice). Each pixel may have 32-bit grayscale resolution. The intensity value of each pixel is normally expressed in Hounsfield units (HU). Sequential slices may be separated by a constant distance along a z direction (i.e., the scan separation axis). For example, the sequential slices may be separated by a distance in a range of approximately 0.75-2.5 millimeters (mm). According to an embodiment, the scan image is a three-dimensional (3D) grey scale image, for example, with an overall size that depends on the area and/or number of slices scanned.

The present invention is not restricted to any specific scanning technique, and is applicable to electron beam computed tomography (EBCT), multi-detector or spiral scans, or any technique that produces as output a 2D or 3D image representing X-ray absorption.

Figure 1:
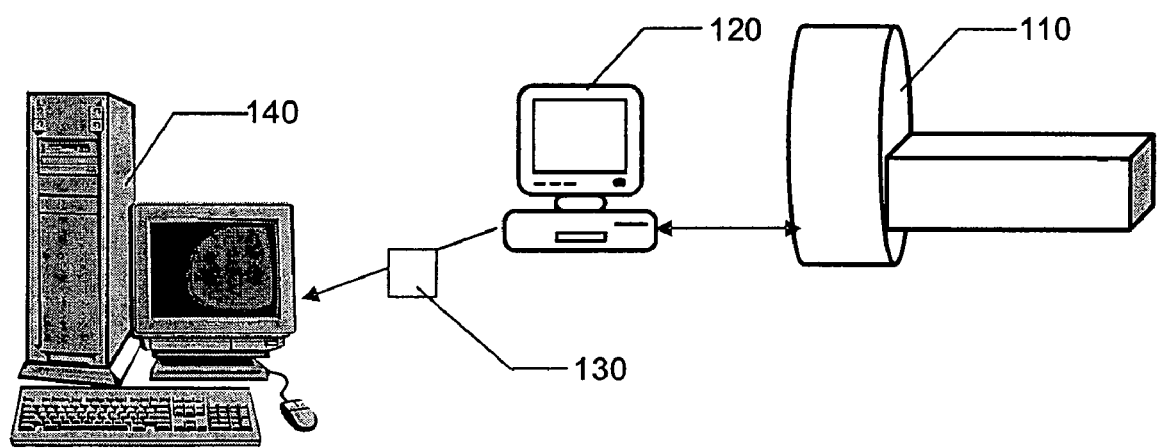
FIG. 1 is a schematic diagram showing a CT scanner and a remote computer for processing image data from the scanner and operating a user interface according to an embodiment of the present invention.

As shown in FIG. 1, the scan image is created by a computer 120. Computer 120 receives scan data from a scanner 110 and constructs the scan image based on the scan data. The scan image is often saved as an electronic file or a series of files which are stored on a storage medium 130, such as a fixed or removable disc. The scan image may be stored in a standard format, such as DIRCOM 3.0, for example. The scan image may be processed by computer 120, or the scan image may be transferred to another computer 140 which runs software for processing and displaying the image as described below. The image processing software may be stored on a computer recordable medium, such as a removable disc, or downloaded over a network. Computer 120 or 140 can be any type of computer system, including but not limited to an example computer system 900 described below with reference to FIG. 9.

User Interface Flowchart

Figure 2:
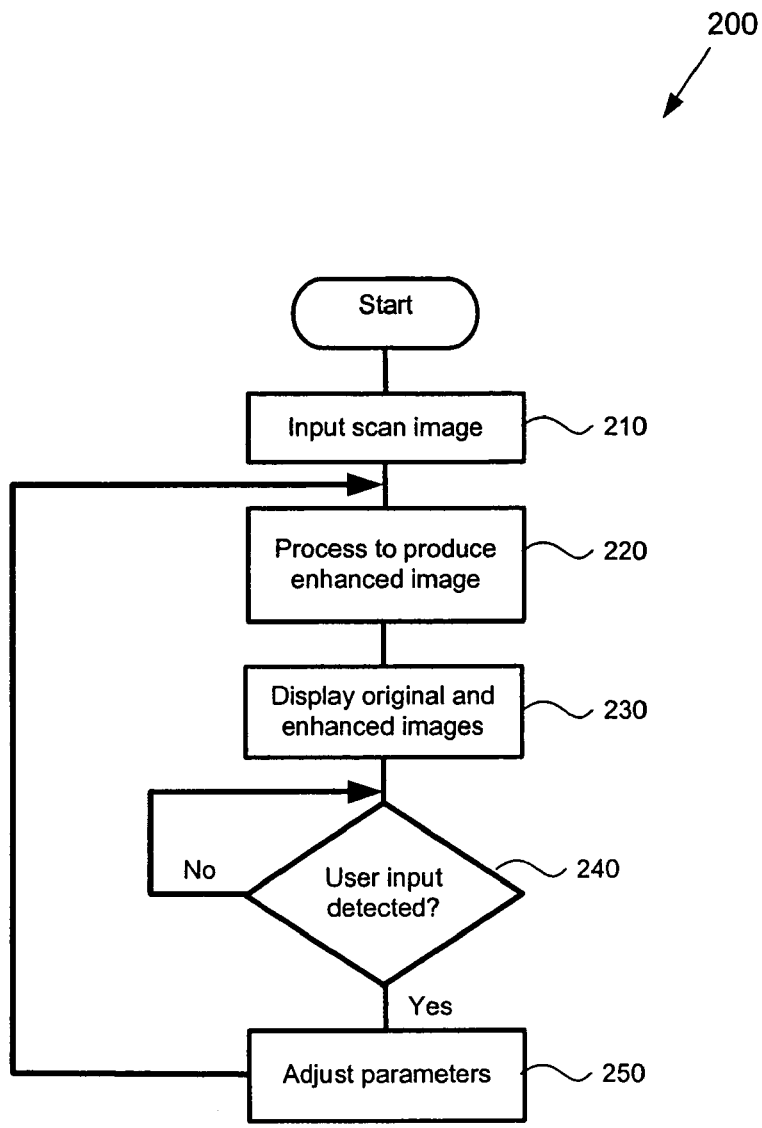
FIG. 2 is a flow chart of the main steps of a method of operating a user interface according to an embodiment of the present invention.

FIG. 2 is a flow chart 200 of the main steps of a method of operating a user interface according to an embodiment of the present invention. An original scan image is provided as input at step 210. The original scan image is processed at step 220 to provide an enhanced scan image. A representation of the original scan image and the enhanced scan image are displayed at step 230. The original and enhanced scan images can be displayed side by side or alternately, to provide some examples.

Parameter values can be associated with the enhanced scan image. The difference between the original scan image and the enhanced scan image can be based on the parameter values. For instance, the parameter values can affect processing the original scan image at step 220. The parameter values can control detection sensitivity or other characteristics of the processing at step 220. A representation of the parameter values can be displayed with the original scan image and/or the enhanced scan image.

If a user input is not detected, as determined at step 240, flow returns to step 240 to determine whether a user input is detected. Step 240 can be repeated until a user input is detected. If a user input is detected at step 240, the parameter values are adjusted at step 250. Flow returns to step 220, where an enhanced scan image is produced using the adjusted parameters.

The original and enhanced scan images may be displayed side by side, or may be displayed alternately at the same position and with the same size and scale, to provide some examples. For instance, the scan images can be displayed alternately by alternately switching on and off the image enhancement. The switching between original and enhanced images may occur in response to the user pressing a specific key or clicking on a button displayed on-screen.

Lung Scan Embodiment

Figure 3:
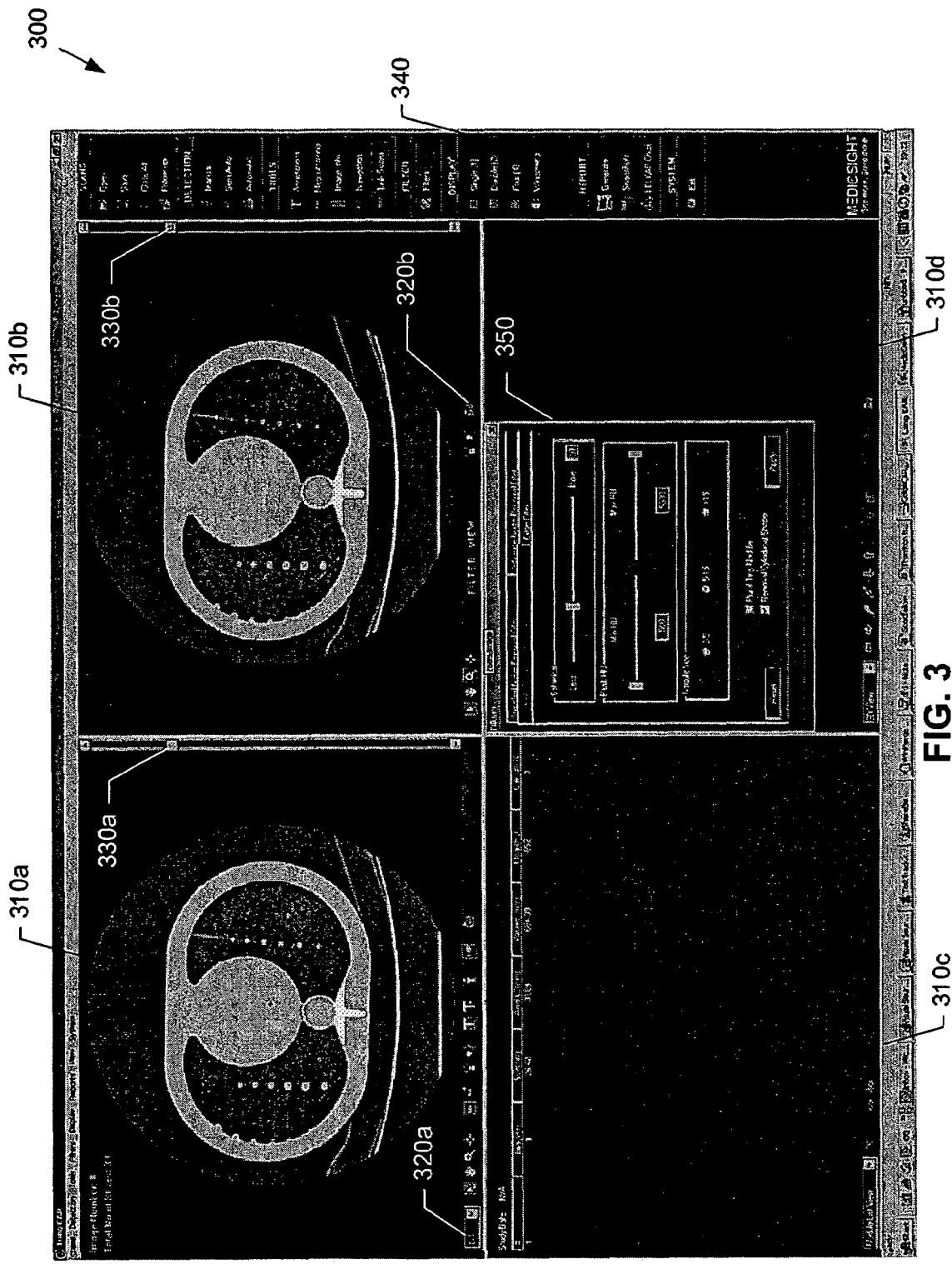
FIG. 3 illustrates a user interface having a sphericity enhancement filter applied according to an embodiment of the present invention.

FIG. 3 illustrates a user interface 300 having a sphericity enhancement filter applied according to an embodiment of the present invention. In the embodiment of FIG. 3, user interface 300 shows a two-dimensional slice of a scan of a lung phantom. A lung phantom is a model that approximates a lung and contains objects having known properties. For example, the lung phantom can be used for testing and/or calibration.

In FIG. 3, user interface 300 is shown in a window that includes four panes 310a-d, though the scope of the invention is not limited in this respect. The window can include any suitable number of panes 310. An original image pane 310a displays a slice of the original scan image. A first toolbar 320a is located at the bottom of original image pane 310a for illustrative purposes. First toolbar 320a includes buttons that allow the user to manipulate the original scan image. First toolbar 320a can facilitate zooming, panning, or rotating the original image, to provide some examples.

Original image pane 310a can include a first scroll bar 330a. For example, first scroll bar 330a can allow the user to scroll up or down within a slice of the original scan image. In another example, first scroll bar 330a can allow the user to move forward and/or backward between slices of the original scan image.

An enhanced image pane 310b displays a slice of the enhanced scan image, which is a version of the original image processed by one or more filters so as to highlight features of the original scan image. In the embodiment of FIG. 3, a sphericity enhancement filter is applied, and objects satisfying the sphericity filter are circled. A second toolbar 320b in enhanced image pane 310b includes buttons that allow the user to manipulate the enhanced scan image. The enhanced scan image can be manipulated by zooming, panning, or rotating the enhanced scan image, to provide some examples. Enhanced image pane 310b includes a second scroll bar 330b to allow the user to scroll up or down within a slice of the enhanced scan image or to move forward and/or backward between slices of the enhanced scan image.

First and second toolbars 320 may be linked so that an image manipulation performed using either toolbar 320 has a corresponding (e.g., equivalent) effect on both the original scan image and the enhanced scan image. For instance, a side-by-side comparison may be made between corresponding views of the original and enhanced scan images. For example, magnifying the original scan image using first toolbar 320a can magnify the enhanced scan image in enhanced image pane 310b by an amount corresponding to the magnification of the original scan image. In another example, magnifying the enhanced scan image using second toolbar 320b can magnify the original scan image in original image pane 310a by the same amount that the enhanced scan image is magnified in enhanced image pane 310b.

First and second scroll bars 330 may be linked, so that moving either scrollbar 330 has a corresponding (e.g., equivalent) effect on both the original scan image and the enhanced scan image. Linking first and second scroll bars 330 can allow the user to move back and forth in the z-direction while comparing the original and enhanced scan images.

The window in which user interface 300 is shown includes a right-hand toolbar 340. Right-hand toolbar 340 displays options that are selectable by the user. In the embodiment of FIG. 3, options are categorized into seven categories (Scans, Detector, Tools, Filter, Display, Report, and System) for illustrative purposes. For instance, the Display category includes options that allow the user to control how many panes 310 are displayed in the window in which the user interface is shown. The options in the Display category are Single, Double, Four, and Windowing. The window includes the number of panes 310 indicated by the option. For example, the window includes two panes 310 if the Double option is selected. In another example, panes 310 are displayed as separate windows if the Windowing option is selected.

In FIG. 3, only two panes 310a and 310b are used for displaying scan images, though the scope of the invention is not limited in this respect. Any suitable number of panes 310 can be used for displaying images. In the embodiment of FIG. 3, third and fourth panes 310c and 310d provide a data display function and a 3-dimensional (3D) nodule display function, respectively, for illustrative purposes.

One or more of the options shown in right-hand toolbar 340 can be associated with sub-options. For example, selecting the Filters option in the Filter category of right-hand toolbar 340 can allow the user to select from multiple filter sub-options, as shown in filter window 350. The Filters option is highlighted in right-hand toolbar 340 to indicate that the user selected the Filters option. Filter window 350 including the filter sub-options can appear in response to the user selecting the Filter option. In FIG. 3, the filter sub-options include Standard Noise Removal Filter, Advanced Noise Removal Filter, Spherical Enhancement Filter, and Edge Filter, each of which is indicated by a separate tab. The user can select a filter sub-option by selecting the corresponding tab. Accordingly, the user can select the type of filter to be applied to the original scan image by selecting the tab that corresponds with the associated filter sub-option. The filter sub-options can include any suitable type of filter. The Filter option need not necessarily be associated with sub-options.

The user can manipulate enhancement parameters associated with each of the filter sub-options. The user clicks the Apply button in filter window 350 to apply the filter associated with the selected filter sub-option. The enhanced image is updated based on the enhancement parameters of the filter selected by the user.

Filter window 350, filter sub-options and enhancement parameters associated therewith are described in greater detail below with reference to FIGS. 4-7.

Sphericity Enhancement Filter

Figure 4:
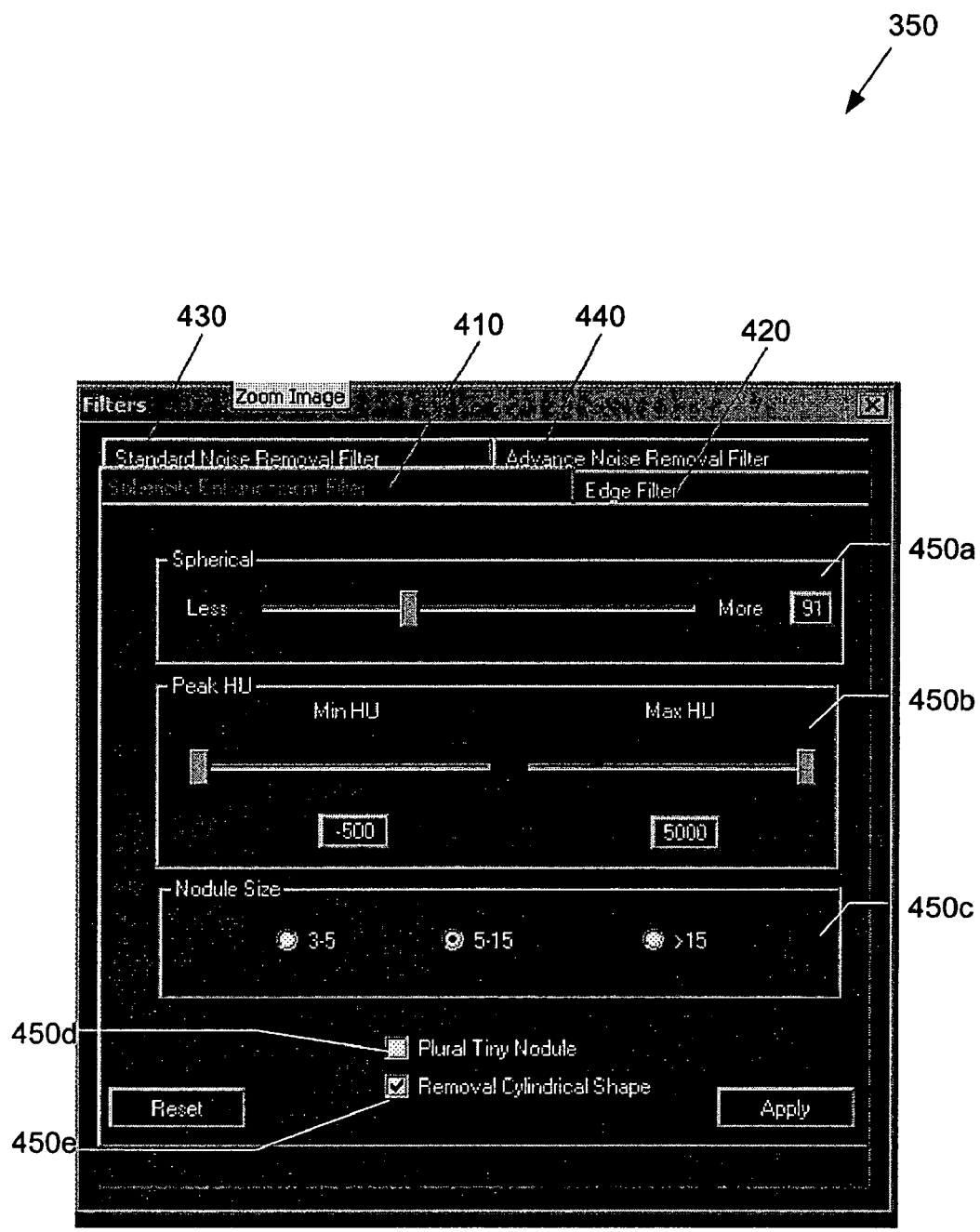
FIG. 4 shows a filter window of a user interface having a sphericity enhancement filter selected according to an embodiment of the present invention.

FIG. 4 shows filter window 350 of FIG. 3 having a sphericity enhancement filter selected according to an embodiment of the present invention. Referring to FIG. 4, a Sphericity Enhancement Filter tab 410 is highlighted to indicate that the user selected the Sphericity Enhancement Filter sub-option. Filter window 350 having the Sphericity Enhancement Filter sub-option selected includes controls 450 for manipulating enhancement parameters associated with the Sphericity Enhancement Filter sub-option. In the embodiment of FIG. 4, filter window 350 includes a Spherical control 450a, a Peak Hounsfield units (HU) control 450b, a Nodule Size control 450c, a Plural Tiny Nodule control 450d, and a Remove Cylindrical Shape control 450e.

Spherical control 450a includes a slider that allows the user to select a minimum level of sphericity for objects passed by the filter. Peak HU control 450b includes a Min HU slider and a Maax HU slider. The Min HU and Max HU sliders allow the user to select a minimum peak intensity and a maximum peak intensity, respectively, within an object to be passed by the filter. Nodule Size control 450c allows the user to select one of a plurality of different size ranges of objects to be passed by the filter. Plural Tiny Nodule control 450d allows the user to select whether to detect plural tiny nodules in a scan image. Remove Cylindrical Shape control 450e allows the user to select whether to remove cylindrical shapes from the scan image. For instance, Remove Cylindrical Shape control 450e can provide the user with the ability to avoid enhancement of spherical shapes that are within cylindrical structures, such as blood vessels.

The Sphericity Enhancement Filter can analyze each volume element (voxel) in a scan image and compare each voxel with surrounding voxels of similar intensity to derive a 3-dimensional (3D) curvature of a surface of equal intensity. Surfaces having a sphericity exceeding a value selected by the user (based on Spherical control 450a) are identified as belonging to spherical objects. Voxels contained within those surfaces are grouped together as parts of the same object. Once all such objects have been identified, those having a maximum intensity between the Min HU and Max HU selected by the user (based on Peak HU control 450b), and a size within the range selected by the user (based on Nodule Size control 450c), are highlighted by the filter.

If a spherical object passed by the filter occupies multiple consecutive slices, the object may be highlighted only on the slice that includes the greatest area of the object.

Edge Enhancement Filter

Figure 5:
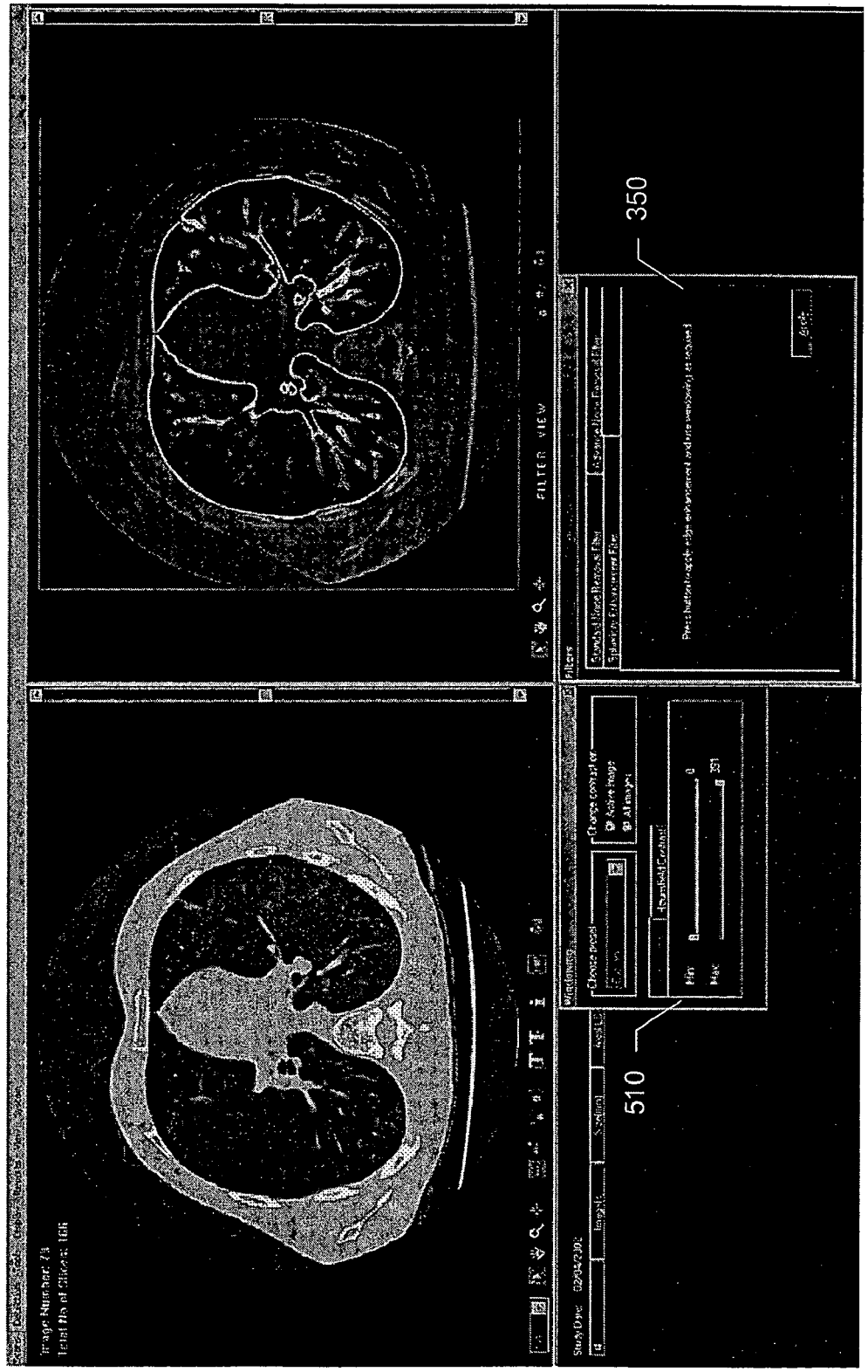
FIG. 5 illustrates a user interface having an edge enhancement filter applied according to an embodiment of the present invention.

FIG. 5 illustrates user interface 300 having an edge enhancement filter applied according to an embodiment of the present invention. Referring to FIG. 5, an Edge Filter tab 420 is highlighted to indicate that the user selected the Edge Filter sub-option. The Edge Filter sub-option can facilitate identifying signs of interstitial disease such as reticulation. In the embodiment of FIG. 5, filter window 350 having the Edge Filter sub-option selected does not include controls for manipulating edge enhancement parameters. A contrast setting window 510 can appear in response to the user selecting Edge Filter tab 420. Contrast setting window 510 can allow the user to vary contrast parameters of the edge enhancement filter. According to an embodiment, edge enhancement is applied to a lung parenchyma area only.

Standard Noise Removal Filter

Figure 6:
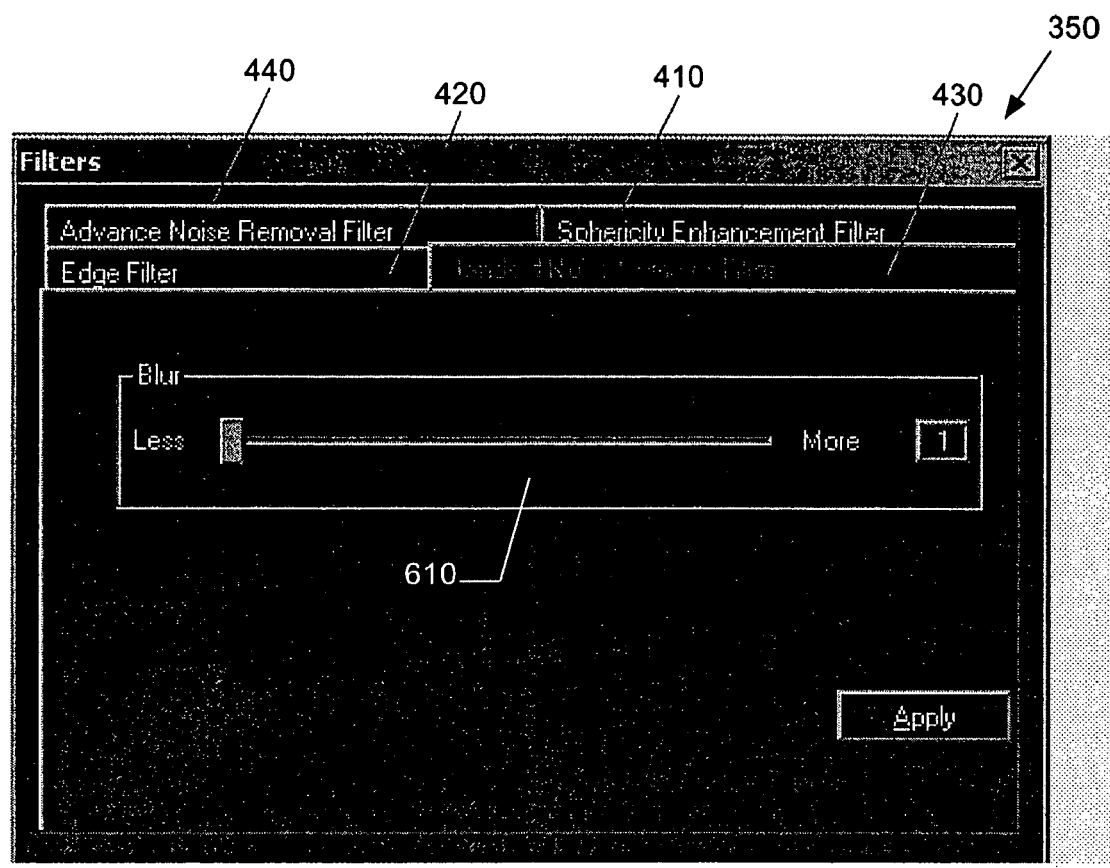
FIG. 6 shows a filter window of a user interface having a standard noise removal filter selected according to an embodiment of the present invention.

FIG. 6 shows filter window 350 having a standard noise removal filter selected according to an embodiment of the present invention. Referring to FIG. 6, a Standard Noise Removal Filter tab 430 is highlighted to indicate that the user selected the Standard Noise Removal Filter sub-option. Filter window 350 having the Standard Noise Removal Filter sub-option selected includes a Blur control 610 for manipulating enhancement parameters associated with the Standard Noise Removal Filter sub-option.

Blur control 610 includes a slider that allows the user to vary the degree of noise smoothing to be applied to a scan image. The standard noise removal filter is advantageous for reading low-dose Multiple Source Correlator Tracker (MSCT) studies, where radiation dose reduction can be achieved at the expense of increased background noise. The standard noise removal filter is used in a standard noise reduction technique to smooth the background noise to the degree set by the user.

Advanced Noise Removal Filter

Figure 7:
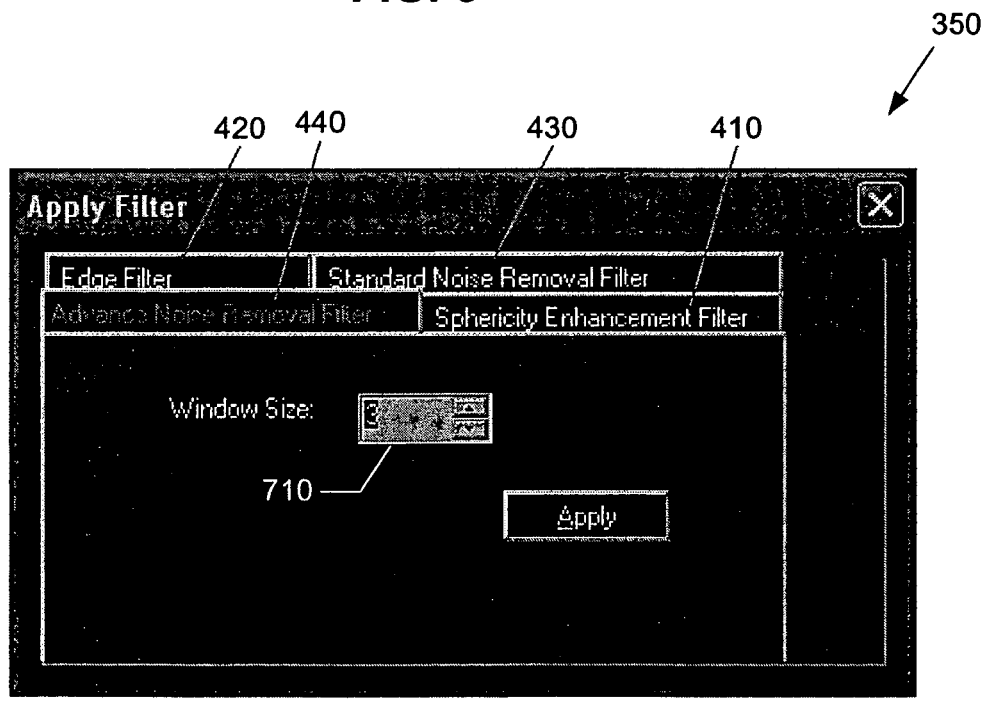
FIG. 7 shows a filter window of a user interface having an advanced noise removal filter selected according to an embodiment of the present invention.

FIG. 7 shows filter window 350 having an advanced noise removal filter selected according to an embodiment of the present invention. An Advanced Noise Removal Filter tab 440 is highlighted in FIG. 7 to indicate that the user selected the Advanced Noise Removal Filter sub-option. Filter window 350 having the Advanced Noise Removal Filter sub-option selected includes a window size selector 710 to allow the user to select the size of the window used to display information relating to an advanced noise reduction technique. The advanced noise reduction technique includes using the advanced noise removal filter to reduce noise associated with a scan image. For instance, the advanced noise reduction technique can provide less apparent blurring, as compared to the standard noise reduction technique described above with respect to FIG. 6. The advanced noise reduction technique may be more time consuming than the standard noise reduction technique.

Colon Scan Embodiment

Figure 8:
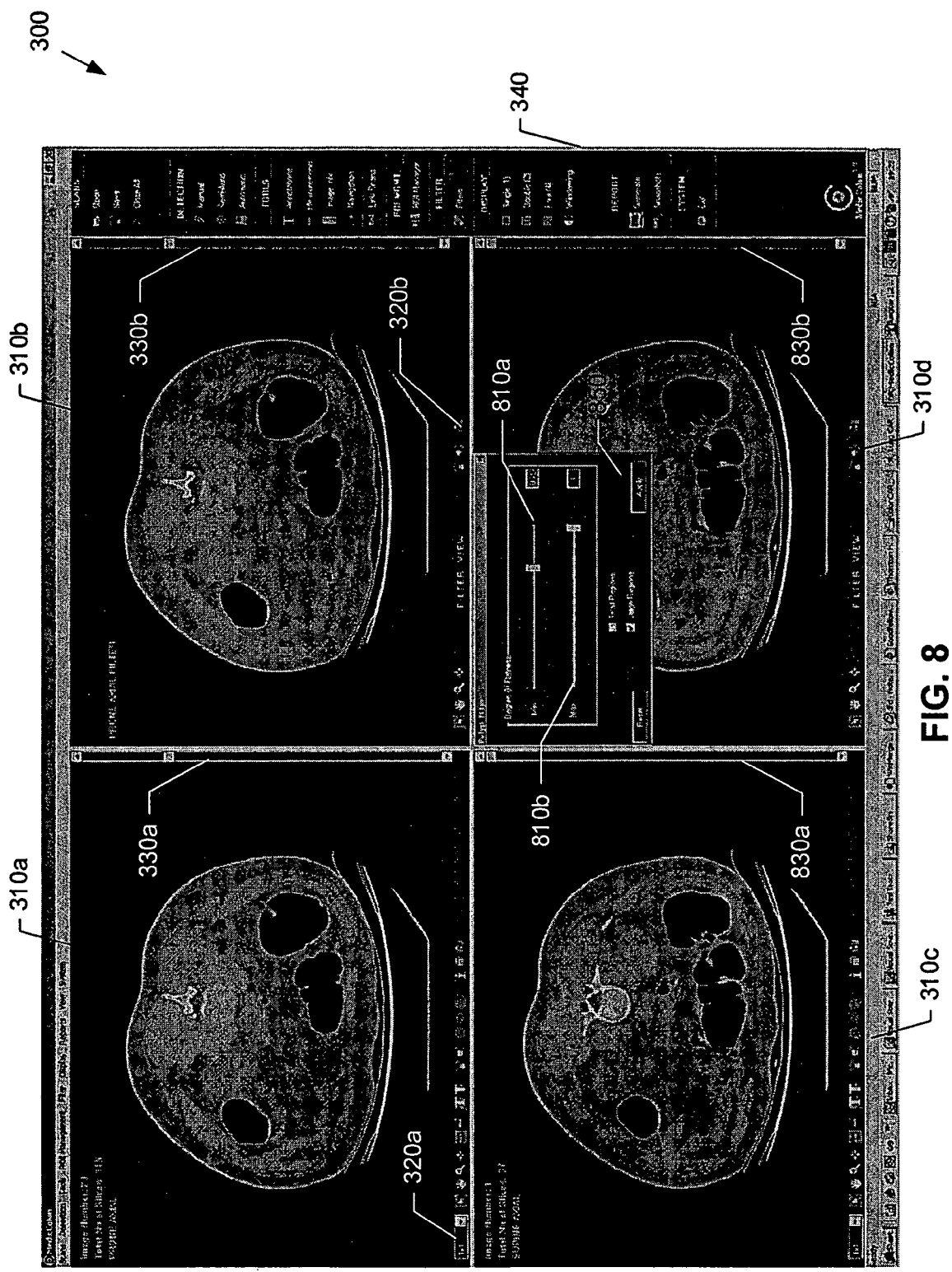
FIG. 8 illustrates a user interface for use with colon scan images according to an embodiment of the present invention.

FIG. 8 illustrates user interface 300 being used with scan images of a colon according to an embodiment of the present invention. Different types of scan images can be associated with different types of filters. For example, FIGS. 3-7, which are associated with the lung embodiment, show filter window 350 having different filter sub-options than filter window 850 shown in FIG. 8, which is associated with the colon scan embodiment.

In the embodiment of FIG. 8, a single polyp filter is available, rather than the choice of filters available in the lung scan embodiment. Filters available in different embodiments need not necessarily be different. For instance, any of the filters available in the lung scan embodiment may be available in the colon scan embodiment, and vice versa. Some elements shown in FIG. 8 are similar to corresponding elements of FIG. 3 and share common reference numerals. Descriptions of these elements are not repeated with reference to FIG. 8.

Filter window 850 displays settings for the polyp filter. The polyp filter highlights raised objects with a spherical element, but does not highlight objects that are elongated and likely to be folds. Filter window 850 includes minimum and maximum flatness sliders 810a and 810b, respectively, which allow the user to select the degree of flatness (or a range thereof) of an object to be highlighted. For example, an object can be highlighted if the degree of flatness of the object is greater than a first degree specified by minimum flatness slider 810a and less than a second degree specified by maximum flatness slider 810b.

In the embodiment of FIG. 8, user interface 300 includes a second original image pane 310c and a second enhanced image pane 310d. Second original image pane 310c and original image pane 310a show a supine axial view and a prone axial view, respectively, of the original scan image. Second enhanced image pane 310d and enhanced image pane 310b show a supine axial view and a prone axial view, respectively, of the enhanced scan image. Toolbars 830a and 830b of second original image pane 310c and second enhanced image pane 310d, respectively, can be linked, such that a change made in one of second original image pane 310c and second enhanced image pane 310d is also made in the other.

Toolbars 330, 830 of any one or more image panes 310 can be linked, such that manipulating a toolbar 330, 830 to provide a change in one pane can result in a corresponding change in the other of the any one or more image panes 310.

Single View Embodiment

As an alternative to the side-by-side views described above with reference to FIGS. 3, 5, and 8, the user may select a display mode in which only a single scan image view is displayed in the user interface window. For instance, the enhancement selected in the filter window can be switched on and/or off by the user, for example, by toggling a button in the filter window. Image display parameters can remain unchanged when switching between the original scan image and the enhanced scan image, which can allow the user to easily compare the original scan image and the enhanced scan image.

Example Computer System

Figure 9:
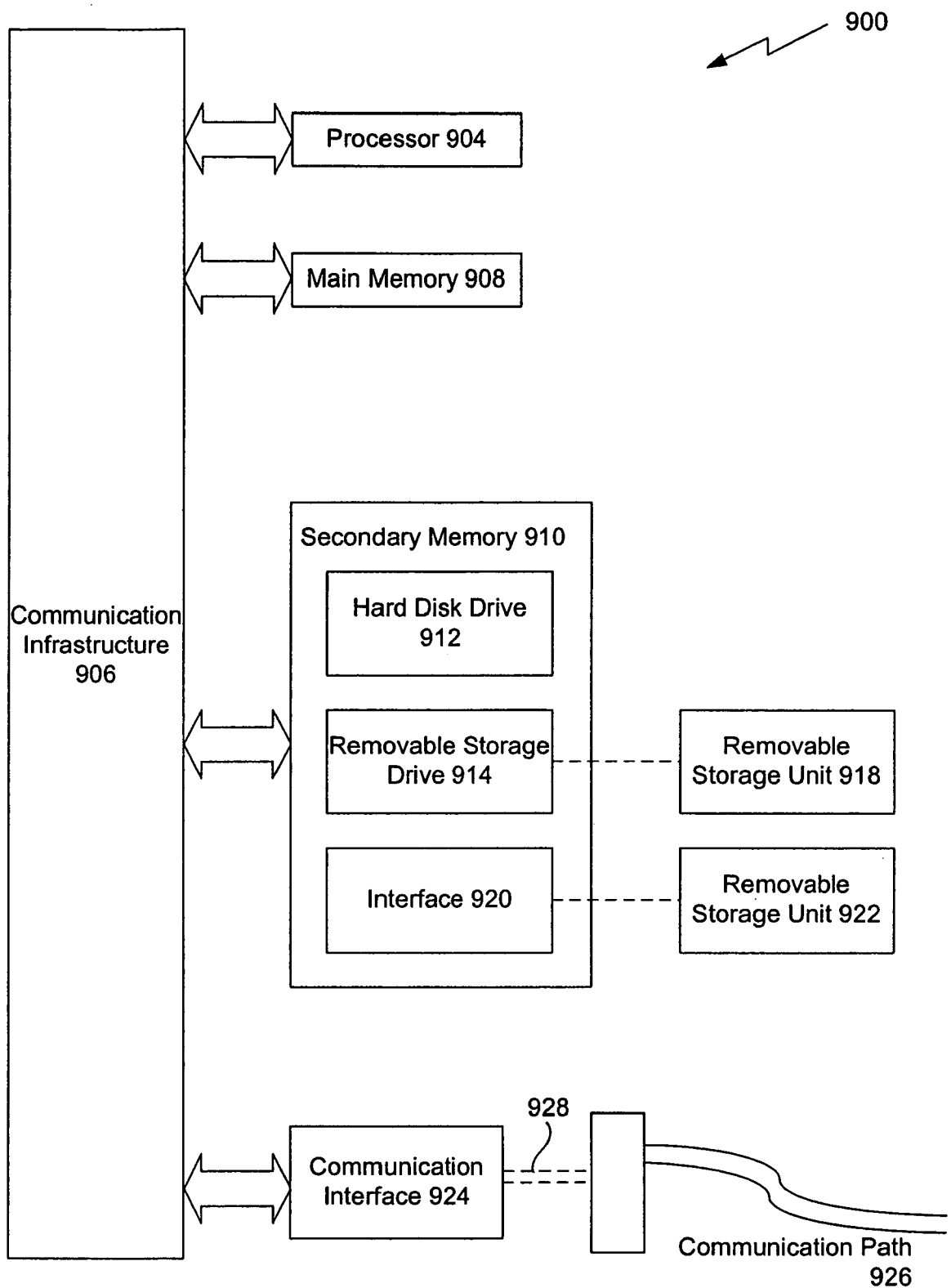
FIG. 9 illustrates an example computer system 900, in which the present invention may be implemented as programmable code.

FIG. 9 illustrates an example computer system 900, in which the present invention may be implemented as programmable code. Various embodiments of the invention are described in terms of this example computer system 900. After reading this description, it will become apparent to a person skilled in the art how to implement the invention using other computer systems and/or computer architectures.

Computer system 900 includes one or more processors, such as processor 904. Processor 904 may be any type of processor, including but not limited to a special purpose or a general purpose digital signal processor. Processor 904 is connected to a communication infrastructure 906 (for example, a bus or network). Various software implementations are described in terms of this exemplary computer system. After reading this description, it will become apparent to a person skilled in the art how to implement the invention using other computer systems and/or computer architectures.

Computer system 900 also includes a main memory 908, preferably random access memory (RAM), and may also include a secondary memory 910. Secondary memory 910 may include, for example, a hard disk drive 912 and/or a removable storage drive 914, representing a floppy disk drive, a magnetic tape drive, an optical disk drive, etc. Removable storage drive 914 reads from and/or writes to a removable storage unit 918 in a well known manner. Removable storage unit 918 represents a floppy disk, magnetic tape, optical disk, etc., which is read by and written to by removable storage drive 914. As will be appreciated, removable storage unit 918 includes a computer usable storage medium having stored therein computer software and/or data.

In alternative implementations, secondary memory 910 may include other similar means for allowing computer programs or other instructions to be loaded into computer system 900. Such means may include, for example, a removable storage unit 922 and an interface 920. Examples of such means may include a program cartridge and cartridge interface (such as that found in video game devices), a removable memory chip (such as an EPROM, or PROM) and associated socket, and other removable storage units 922 and interfaces 920 which allow software and data to be transferred from removable storage unit 922 to computer system 900.

Computer system 900 may also include a communication interface 924. Communication interface 924 allows software and data to be transferred between computer system 900 and external devices. Examples of communication interface 924 may include a modem, a network interface (such as an Ethernet card), a communication port, a Personal Computer Memory Card International Association (PCMCIA) slot and card, etc. Software and data transferred via communication interface 924 are in the form of signals 928 which may be electronic, electromagnetic, optical, or other signals capable of being received by communication interface 924. These signals 928 are provided to communication interface 924 via a communication path 926. Communication path 926 carries signals 928 and may be implemented using wire or cable, fiber optics, a phone line, a cellular phone link, a radio frequency link, or any other suitable communication channel. For instance, communication path 926 may be implemented using a combination of channels.

In this document, the terms "computer program medium" and "computer usable medium" are used generally to refer to media such as removable storage drive 914, a hard disk installed in hard disk drive 912, and signals 928. These computer program products are means for providing software to computer system 900.

Computer programs (also called computer control logic) are stored in main memory 908 and/or secondary memory 910. Computer programs may also be received via communication interface 924. Such computer programs, when executed, enable computer system 900 to implement the present invention as discussed herein. Accordingly, such computer programs represent controllers of computer system 900. Where the invention is implemented using software, the software may be stored in a computer program product and loaded into computer system 900 using removable storage drive 914, hard disk drive 912, or communication interface 924, to provide some examples.

In alternative embodiments, the invention can be implemented as control logic in hardware, firmware, or software or any combination thereof.

The embodiments above are described by way of example, and are not intended to limit the scope of the invention. Various alternatives may be envisaged which nevertheless fall within the scope of the claims. As will be apparent from the above discussion, the method can be performed using a 2D image having a single CT slice, or a 3D image having consecutive CT slices.

CONCLUSION

Example embodiments of the methods, systems, and components of the present invention have been described herein. As noted elsewhere, these example embodiments have been described for illustrative purposes only, and are not limiting. Other embodiments are possible and are covered by the invention. Such other embodiments will be apparent to persons skilled in the relevant art(s) based on the teachings contained herein. Thus, the breadth and scope of the present invention should not be limited by any of the above described exemplary embodiments, but should be defined only in accordance with the following claims and their equivalents.

What is claimed is:

1. A computer-implemented method of displaying a computed tomography (CT) scan image, comprising:
    a) receiving a user input to modify one or more parameters associated with a filter, to provide one or more user-modified parameters;
    b) modifying the filter based on the one or more user-modified parameters, to provide a modified filter;
    c) processing the scan image using the modified filter to generate an enhanced scan image in which features indicative of an abnormality are enhanced and at least one feature of the scan image is obscured; and
    d) displaying a view of the scan image and a corresponding view of the enhanced scan image so as to enable a visual comparison between the scan image and the enhanced scan image.

2. The method of claim 1, wherein the view of the scan image and the corresponding view of the enhanced scan image are displayed simultaneously.

3. The method of claim 1, wherein the view of the scan image and the corresponding view of the enhanced scan image are displayed alternately.

4. The method of claim 3, wherein the display alternates between the view of the scan image and the view of the enhanced scan image in response to a user input.

5. The method of claim 3, wherein the scan image and the corresponding view of the enhanced scan image are displayed alternately in a substantially similar position.

6. The method of claim 1, including receiving a user input for modifying the view, and modifying the displayed view of the scan image and the view of the enhanced scan image correspondingly in response to the user input.

7. The method of claim 6, wherein the user input is for selecting a slice of the scan image, and the selected slice of both the scan image and the enhanced image are displayed in response to the user input.

8. The method of claim 1, further comprising receiving a user input for selecting a selectable filter of a plurality of selectable filters, wherein modifying the filter includes modifying the selected selectable filter and processing the scan image includes processing the scan image using the selectable filter.

9. The method of claim 1, wherein processing the scan image includes processing the scan image of a lung using a sphericity enhancement technique.

10. The method of claim 1, wherein processing the scan image includes processing the scan image of a lung using an edge enhancement technique.

11. The method of claim 1, wherein processing the scan image includes processing the scan image of a colon by enhancing spherical objects raised from a wall of the colon.

12. An article comprising a medium for storing instructions to enable a processor-based system to:
  a) receive a user input to modify one or more user-modifiable parameters associated with a filter, to provide one or more user-modified parameters;
  b) modify the filter based on the one or more user-modified parameters, to provide a modified filter;
  c) process the scan image using the modified filter to generate an enhanced scan image in which features indicative of an abnormality are enhanced and at least one feature of the scan image is obscured; and
  d) output for display a view of the scan image and a corresponding view of the enhanced scan image so as to enable a visual comparison between the scan image and the enhanced scan image.

13. An apparatus to display a computed tomography (CT) scan image, comprising:
  a) means for receiving a user input to modify one or more user-modifiable parameters associated with a filter, to provide one or more user-modified parameters;
  b) means for modifying the filter based on the one or more user-modified parameters, to provide a modified filter;
  c) means for processing the scan image using the modified filter to generate an enhanced scan image in which features indicative of an abnormality are enhanced and at least one feature of the scan image is obscured; and
  d) means for outputting for display a view of the scan image and a corresponding view of the enhanced scan image so as to enable a visual comparison between the scan image and the enhanced scan image.

14. A system for displaying a computed tomography (CT) scan image, comprising:
  a) a user input device for receiving a user input to modify one or more user-modifiable parameters associated with a filter, to provide one or more user-modified parameters; and
  b) a processor for modifying the filter based on the one or more user-modified parameters to provide a modified filter, for processing the scan image using the modified filter to generate an enhanced scan image in which features indicative of an abnormality are enhanced and at least one feature of the scan image is obscured, and for outputting for display a view of the scan image and a corresponding view of the enhanced scan image so as to enable a visual comparison between the scan image and the enhanced scan image.

* * * * *